United States Patent
Aizawa et al.

(10) Patent No.: US 9,783,480 B2
(45) Date of Patent: Oct. 10, 2017

(54) PHENYL (METH)ACRYLATE PRODUCTION METHOD AND PHENYL (METH)ACRYLATE COMPOSITION

(71) Applicant: Mitsubishi Chemical Corporation, Tokyo (JP)

(72) Inventors: Ryo Aizawa, Otake (JP); Takeshi Matsuo, Otake (JP); Naoshi Murata, Otake (JP); Hiroyuki Mori, Otake (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 15/284,750

(22) Filed: Oct. 4, 2016

(65) Prior Publication Data

US 2017/0022136 A1    Jan. 26, 2017

Related U.S. Application Data

(62) Division of application No. 15/025,507, filed as application No. PCT/JP2014/078338 on Oct. 24, 2014.

(30) Foreign Application Priority Data

Oct. 30, 2013  (JP) ................. 2013-225352

(51) Int. Cl.
| | |
|---|---|
| C07C 67/11 | (2006.01) |
| C07C 57/62 | (2006.01) |
| C07C 67/10 | (2006.01) |
| C07C 57/42 | (2006.01) |
| C07C 67/62 | (2006.01) |

(52) U.S. Cl.
CPC ............. C07C 57/42 (2013.01); C07C 67/10 (2013.01); C07C 67/11 (2013.01); C07C 67/62 (2013.01)

(58) Field of Classification Search
CPC ................. C07C 67/11; C07C 67/62
See application file for complete search history.

(56) References Cited

U.S. PATENT DOCUMENTS

| | | | |
|---|---|---|---|
| 6,548,678 B1 | 4/2003 | Yamamoto et al. | |
| 2003/0028051 A1 | 2/2003 | Shibusawa et al. | |
| 2004/0267045 A1 | 12/2004 | Yada et al. | |

FOREIGN PATENT DOCUMENTS

| | | | |
|---|---|---|---|
| GB | 902132 A | | 7/1962 |
| JP | 41-17748 B1 | | 10/1966 |
| JP | 5-286894 A | | 11/1993 |
| JP | 7-126213 A | | 5/1995 |
| JP | 2003-89672 A | | 3/2003 |
| JP | 2003-104974 A | | 4/2003 |
| JP | 2003-226667 A | | 8/2003 |
| JP | 2003-252830 A | | 9/2003 |
| JP | 2007-246503 A | | 9/2007 |
| JP | 2007246503 A | * | 9/2007 |
| JP | 2011-105667 A | | 6/2011 |

OTHER PUBLICATIONS

Extended European Search Report dated Sep. 27, 2016 in Patent Application No. 14859028.4.
Fulga Tanasa, et al., "Syntheses of Esters from Carboxylic Acids and Diphenyl Carbonate-4-Dimethylaminopyridine at Room Temperature" vol. 35, No. 38, XP055304149, Sep. 21, 2014, 1 Page.
Allen R. Banks, et al., "A Convenient Synthesis of Methacrylates," Journal of Organic Chemistry, vol. 42, No. 24, 1977, (2 pages).
Eric A. Gunnewegh, et al., "Zeolite catalyzed synthesis of coumarin derivatives," Journal of Molecular Catalysis A: Chemical 100, 1995, pp. 87-92.
International Search Report dated Jan. 20, 2015 in PCT/JP2014/078338 filed Oct. 24, 2014.

* cited by examiner

*Primary Examiner* — Paul A Zucker
(74) *Attorney, Agent, or Firm* — Oblon, McClelland, Maier & Neustadt, L.L.P.

(57) ABSTRACT

Provided is a method that can produce phenyl(meth)acrylate inexpensively and at high yields. The phenyl(meth)acrylate production method of the present invention reacts (meth)acrylic acid with carbonic acid diphenyl. Further, the phenyl (meth)acrylate composition of the present invention contains 90-99.999 wt % phenyl(meth)acrylate and 0.001-10% carbonic acid diphenyl. Or, the phenyl(meth)acrylate composition of the present invention contains 90-99.999 wt % phenyl(meth)acrylate and 0.001-10 wt % of a specified compound.

10 Claims, No Drawings

PHENYL (METH)ACRYLATE PRODUCTION METHOD AND PHENYL (METH)ACRYLATE COMPOSITION

The present application is a Divisional of U.S. application Ser. No. 15/025,057, filed Mar. 28, 2016, now pending; which is a 371 of PCT/JP2014/078338, filed Oct. 24, 2014; and is based upon and claims the benefit of priority to Japanese Patent Application No. 2013-225352, filed Oct. 30, 2013. The entire contents of the application are incorporated herein by reference.

FIELD OF THE INVENTION

The present invention relates to a phenyl (meth)acrylate production method and a phenyl (meth)acrylate composition.

BACKGROUND ART

Several methods have been proposed for producing phenyl (meth)acrylate (for example, Patent Literature 1 and 2, Non-Patent Literature 1).

Patent Literature 1 discloses a method for dehydrating (meth)acrylic acid and phenol in the presence of an acidic catalyst. Patent Literature 2 discloses a method for reacting (meth)acrylate and diphenyl carbonate. Non-Patent Literature 1 discloses a method for reacting (meth)acrylic acid chloride and phenol in the presence of amine.

PRIOR ART LITERATURE

Patent Literature

Patent Literature 1: JP2011-105667A
Patent Literature 2: JP2007-246503A

Non-Patent Literature

Non-Patent Literature 1: Journal of Organic Chemistry 1977, 42, 3965

SUMMARY OF THE INVENTION

Problems to be Solved by the Invention

However, when the method described in Patent Literature 1 is employed, since phenyl (meth)acrylate decomposes by the water generated through reactions, it is hard to have the reaction equilibrium incline to production, and thus phenyl (meth)acrylate cannot be synthesized efficiently. When the method in Patent Literature 2 is employed, since an extra amount of (meth)acrylate relative to diphenyl carbonate is necessary, the amount of phenyl (meth)acrylate to be produced per unit volume of reactor is less. Also, when the method in Non-Patent Literature 1 is employed, the reaction apparatus may corrode by hydrogen chloride derived from (meth)acrylic acid chloride used as a raw material. In addition, since (meth)acrylic acid chloride is expensive, the production cost of phenyl (meth)acrylate increases.

Accordingly, the objective of the present invention is to provide a method for producing phenyl (meth)acrylate at a reasonable cost and a higher yield.

Solutions to the Problems

The inventors of the present invention have conducted extensive studies on problems of conventional technologies and have found that the above-described objective is achieved by reacting (meth)acrylic acid and diphenyl carbonate, and the present invention has been completed accordingly. Namely, the present invention is shown as described in the following [1] through [13].

[1] A method for producing phenyl (meth)acrylate through reactions of (meth)acrylic acid and diphenyl carbonate.

[2] The method for producing phenyl (meth)acrylate described in [1], in which (meth)acrylic acid and diphenyl carbonate are reacted in the presence of a catalyst

[3] The method for producing phenyl (meth)acrylate described in [2], in which the catalyst is at least one type selected from among nitrogen-containing organic compounds, Group 1 metal compounds, Group 2 metal compounds, and metal trifluoromethanesulfonates.

[4] The method for producing phenyl (meth)acrylate described in [3], in which the catalyst is a nitrogen-containing organic compound represented by formula (1) or (2) below.

[chemical formula 1]

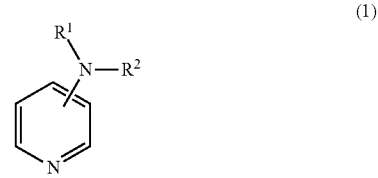

(1)

(In formula (1), the $NR^1R^2$ group is bonded to any site among 2, 3 and 4 positions of a pyridine ring. $R^1$ and $R^2$ are independently a hydrogen atom, a substituted or unsubstituted alkyl group having 1~30 carbon atoms, a substituted or unsubstituted alkenyl group having 2~30 carbon atoms, or a substituted or unsubstituted aryl group having 6~30 carbon atoms. $R^1$ and $R^2$ may be bonded to form a ring.)

[chemical formula 2]

(2)

(In formula (2), $R^3$ is a hydrogen atom, substituted or unsubstituted alkyl group having 1~30 carbon atoms, a substituted or unsubstituted alkenyl group having 2~30 carbon atoms, or a substituted or unsubstituted aryl group having 6~30 carbon atoms.)

[5] The method for producing phenyl (meth)acrylate described in [3], in which a Group 2 metal compound is a magnesium compound with ion-organic ligands.

[6] The method for producing phenyl (meth)acrylate described in any of [2] through [5], in which the amount of catalyst to be used is set in a range of 0.00001 mol to 4 mol relative to 1 mol of diphenyl carbonate.

[7] The method for producing phenyl (meth)acrylate described in [6], in which the amount of catalyst to be used is set in a range of 0.0001 mol to 0.6 mol relative to 1 mol of diphenyl carbonate.

[8] The method for producing phenyl (meth)acrylate described in [7], in which the amount of catalyst to be used is set in a range of 0.03 mol to 0.15 mol relative to 1 mol of diphenyl carbonate.

[9] The method for producing phenyl (meth)acrylate described in any of [1] through [8], in which the amount of (meth)acrylic acid to be used is set in a range of 0.1 mol to 5 mol relative to 1 mol of diphenyl carbonate.

[10] The method for producing phenyl (meth)acrylate described in [9], in which the amount of (meth)acrylic acid to be used is set in a range of 0.8 mol to 1.6 mol relative to 1 mol of diphenyl carbonate.

[11] The method for producing phenyl (meth)acrylate described in any of [1] through [10], in which (meth)acrylic acid is added by batch or continuously to diphenyl carbonate.

[12] A phenyl (meth)acrylate composition containing phenyl (meth)acrylate in a range of 90 mass % to 99.999 mass %, and diphenyl carbonate in a range of 0.001 mass % to 10 mass %.

[13] A phenyl (meth)acrylate composition containing phenyl (meth)acrylate in a range of 90 mass % to 99.999 mass %, and a compound represented by formula (3) below, and/or a compound represented by formula (4) below, in a range of 0.001 mass % to 10 mass %.

[chemical formula 3]

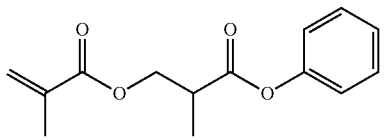

(3)

[chemical formula 4]

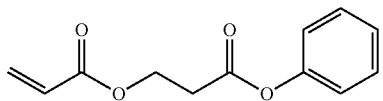

(4)

Effects of the Invention

According to the present invention, phenyl (meth)acrylate is produced at a reasonable cost and a higher yield.

DETAILED DESCRIPTION OF THE EMBODIMENTS

In the method for producing phenyl (meth)acrylate according to the embodiments of the present invention, (meth)acrylic acid and diphenyl carbonate are reacted, that is, (meth)acrylic acid and diphenyl carbonate are used as raw materials and reacted accordingly. In such a method, carbon dioxide is generated as a byproduct, causing nonequilibrium reactions. Accordingly, the raw materials are completely reacted. As a result, using the production method related to the present invention, phenyl (meth)acrylate is produced at a reasonable and a higher yield.

The production method for phenyl (meth)acrylate related to the present invention is described below in detail. In the present application, (meth)acrylic acids mean acrylic acids and/or methacrylic acids. In addition, phenyl (meth)acrylates mean phenyl acrylates and/or phenyl methacrylates. Also, MAA adducts (methacrylic acid adducts) are compounds represented by formula (3) shown above, and AA adducts (acrylic acid adducts) are compounds represented by formula (4) above. In addition, adducts of (meth)acrylic acid mean compounds represented by formula (3) above and/or compounds represented by formula (4) above. Moreover, PhOH adducts (phenol adducts) are compounds represented by formula (5) below. In addition, phenyl methacrylate dimers are compounds represented by formula (6) below, and PHA-PhOH adducts are compounds represented by formula (7) below.

[chemical formula 5]

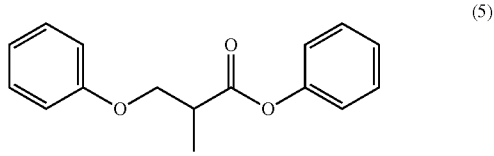

(5)

[chemical formula 6]

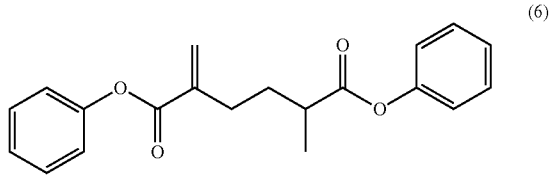

(6)

[chemical formula 7]

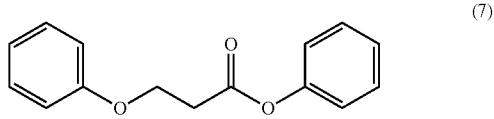

(7)

(1) Diphenyl Carbonate

The purity level of diphenyl carbonate used in the embodiments of the present invention is not limited specifically, but it is preferred to be 50 mass % or higher, more preferably 70 mass % or higher, even more preferably 85 mass % or higher, especially preferably 90 mass % or higher, and most preferably 95 mass % or higher. Diphenyl carbonate with a purity level of 50 mass % or higher can increase the production of phenyl (meth)acrylate per unit volume of reactor.

(2) (Meth)acrylic Acid

The purity level of (meth)acrylic acid used in the embodiments of the present invention is not limited specifically, but it is preferred to be 50 mass % or higher, more preferably 70 mass % or higher, even more preferably 85 mass % or higher, especially preferably 90 mass % or higher, and most preferably 95 mass % or higher. (Meth)acrylic acid with a purity level of 50 mass % or higher can increase the production of phenyl (meth)acrylate per unit volume of reactor.

Methacrylic acid is preferred to be used as (meth)acrylic acid in the embodiments of the present invention. Methacrylic acid can produce phenyl ester at a higher yield in a shorter reaction time.

(3) Catalyst

It is an option to use or not to use a catalyst for reaction of (meth)acrylic acid and diphenyl carbonate, but using a catalyst is preferred because the reaction rate is accelerated. A catalyst to be used is not limited to any specific type, but using nitrogen-containing organic compounds, Group 1 metal compounds, Group 2 metal compounds, metal trifluoromethanesulfonates and the like are preferred from the viewpoint of accelerating the production rate of phenyl (meth)acrylate. Those catalysts may be used alone or in combination thereof.

(3-1) Nitrogen-Containing Organic Compounds

Examples of a nitrogen-containing organic compound are not limited specifically: primary amines such as monomethyl amine, aniline, o-toluidine, and o-anisidine; secondary amines such as dimethylamine, diethylamine, and piperidine; tertiary amines such as trimethylamine, triethylamine, tri-n-propylamine, triisopropylamine, diethylisopropylamine, tri-n-butylamine, triisobutylamine, tri-tert-butylamine, tri-n-octylamine, tri-2-ethylhexylamine, and 1,4-diazabicyclo[2.2.2]octane; and heterocyclic compounds such as pyridine, pyrrole, quinoline, and acridine. In addition, any nitrogen-containing organic compound may have at least two sites in a molecule that are selected from among a primary amine site, secondary amine site, tertiary amine site and nitrogen site of a heterocyclic compound.

Among the nitrogen-containing organic compounds listed above, those having two nitrogen atoms in a molecule are preferred, more preferably those having two or more nitrogen atoms with conjugative interactions. Examples of nitrogen-containing organic compounds are 4-aminopyridine, 4-dimethylaminopyridine, 4-diethylaminopyridine, imidazole, 1-methylimidazole, pyrimidine, and 1,8-diazabicyclo[5.4.0]undec-7-ene.

Among nitrogen-containing organic compounds having at least two nitrogen atoms with conjugative interactions, those represented by formula (1) or (2) above are preferred because such compounds are capable of enhancing the rate of producing phenyl (meth)acrylates. As for $R^1$ and $R^2$ in formula (1), examples of alkyl groups are methyl group, ethyl group, n-propyl group, isopropyl group, n-butyl group, isobutyl group, tert-butyl group, n-octyl group, and 2-ethylhexyl group, and the like. Examples of alkenyl groups are vinyl group, allyl group, 1-butenyl group and the like. Examples of aryl groups are phenyl group, 1-naphthyl group, 2-naphthyl group, 9-anthracenyl group, and the like. Substituents of alkyl groups, alkenyl groups and aryl groups are, for example, fluoro group, chloro group, bromo group, iodine group, methoxy group, ethoxy group, acetyl group, trimethylsilyl group, dimethylphosphino group, nitrile group, nitro group, and the like. When $R^1$ and $R^2$ are bonded to form a ring, examples of bonding types are carbon-carbon bonding, carbon-oxygen bonding, carbon-nitrogen bonding, carbon-sulfur bonding, sulfur-sulfur bonding, carbon-phosphorus bonding, carbon-silicon bonding, and the like. Substituted or unsubstituted alkyl, alkenyl, or aryl groups that represent $R^3$ in formula (3) above may be the same groups that represent $R^1$ and $R^2$ in formula (1).

Examples of nitrogen-containing organic compounds represented by formula (1) above are 2-aminopyridine, 2-(methylamino)pyridine, 2-dimethylaminopyridine, 3-aminopyridine, 3-(methylamino)pyridine, 3-dimethylaminopyridine, 4-aminopyridine, 4-(methylamino)pyridine, 4-dimethylaminopyridine, 4-diethylaminopyridine, 4-anilinopyridine, 4-pyrrolidinopyridine, 4-(4-Pyridyl)morpholine, 4-(4-Aminopiperidino)pyridine, and the like.

Examples of nitrogen-containing organic compounds represented by formula (2) above are imidazole, 1-methylimidazole, 1 ethylimidazole, 1-propylimidazole, 1-isopropylimidazole, 1-butylimidazole, 1-phenylimidazole, and the like.

Among the nitrogen-containing organic compounds represented by formula (1) or (2), it is preferred to use 4-aminopyridine, 4-dimethylaminopyridine, 4-diethylaminopyridine, imidazole, and 1-methylimidazole. It is more preferred to use 4-aminopyridine, 4-dimethylaminopyridine, and 4-diethylaminopyridine. Those compounds listed above may be used alone or in combination thereof.

(3-2) Group 1 Metal Compounds

Group 1 metal compounds are not limited specifically. As Group 1 metals, lithium, sodium and potassium are preferred, more preferably lithium and sodium, even more preferably lithium.

Group 1 metal compounds are preferred to have ligands. Examples of ligands are (meth)acrylic acid ions, formic acid ions, acetic acid ions, acetylacetonate ions, trifluoro-2,4-pentanedionato ions, phenoxy ions, methoxy ions, hydroxide ions, carbonate ions, hydrogen carbonate ions, and the like.

Ligands are preferred to be ionic, more preferably ion-organic ligands from the viewpoint of accelerating the production rate of phenyl (meth)acrylates. Ion-organic ligands are preferred to be those of carboxylic acid ions and aromatic alkoxy ions, more preferably those of (meth)acrylic acid ions and phenoxy ions, even more preferably those of methacrylic acid ions and phenoxy ions.

Examples of Group 1 metal compounds with ion-organic ligands are lithium (meth)acrylate, lithium formate, lithium acetate, lithium phenoxide, lithium methoxide, sodium (meth)acrylate, sodium formate, sodium acetate, sodium phenoxide, sodium methoxide, potassium (meth)acrylate, potassium formate, potassium acetate, potassium phenoxide, potassium methoxide, and the like. Among them, lithium (meth)acrylate, sodium (meth)acrylate, potassium (meth)acrylate, lithium phenoxide, sodium phenoxide, and potassium phenoxide are preferred; more preferably lithium (meth)acrylate, sodium (meth)acrylate, lithium phenoxide, and sodium phenoxide; even more preferably lithium (meth)acrylate and lithium phenoxide; especially preferably lithium methacrylate and lithium phenoxide. They may be used alone or in combination thereof.

(3-3) Group 2 Metal Compounds

Group 2 metal compounds are not limited specifically; as Group 2 metals, beryllium, magnesium, and calcium are preferred, more preferably magnesium and calcium, even more preferably magnesium.

Group 2 metal compounds are preferred to be those having ligands. Ligands may be the same as those in Group 1 metal compounds. Especially, from the viewpoint of accelerating the production rate of phenyl (meth)acrylate, Group 2 metal compounds are preferred to be magnesium compounds with ion-organic ligands.

Examples of Group 2 metal compounds with ion-organic ligands are beryllium (meth)acrylate, beryllium formate, beryllium acetate, beryllium phenoxide, beryllium methoxide, magnesium (meth)acrylate, magnesium formate, magnesium acetate, magnesium phenoxide, magnesium methoxide, magnesium acetylacetonate, bis(trifluoro-2,4-pentanedionato)magnesium, calcium (meth)acrylate, calcium formate, calcium acetate, calcium phenoxide, calcium methoxide, calcium acetylacetonate, bis(trifluoro-2,4-pentanedionato)calcium, and the like. Among those listed above, magnesium (meth)acrylate, calcium (meth)acrylate, magnesium phenoxide, calcium phenoxide, magnesium acetylacetonate, and calcium acetylacetonate are preferred; more preferably magnesium (meth)acrylate, magnesium phenoxide and magnesium acetylacetonate; even more preferably magnesium (meth)acrylate and magnesium phenoxide; especially preferably magnesium methacrylate and magnesium phenoxide. They may be used alone or in combination thereof.

(3-4) Metal Trifluoromethanesulfonates

Metal trifluoromethanesulfonates are not limited specifically. Examples of metals contained in metal trifluoromethanesulfonates are samarium, scandium, lanthanum, cerium, stannum, copper, europium, hafnium, neodymium, nickel, silver, thulium, ytterbium, yttrium, zinc and the like. Among those listed above, samarium, scandium, lanthanum, cerium and hafnium are preferred; more preferably samarium, scandium, and lanthanum even more preferably samarium.

More specifically, preferred metal trifluoromethanesulfonates are samarium trifluoromethanesulfonate, scandium trifluommethanesulfonate, and lanthanum trifluoromethanesulfonate; more preferably samarium trifluoromethanesulfonate. They may be used alone or in combination thereof.

(4) Producing Phenyl (Meth)acrylate

The amount of (meth)acrylic acid used in the embodiments of the present invention is not limited specifically, as long as phenyl (meth)acrylate is efficiently obtained. Relative to 1 mol of diphenyl carbonate, the amount may be set at 0.1 mol or greater, preferably 0.5 mol or greater, more preferably 0.8 mol or greater, even more preferably 0.9 mol, especially preferably 0.95 mol or greater.

In addition, relative to 1 mol of diphenyl carbonate, the amount of (meth)acrylic acid may be set at 5 mol or less, preferably 3 mol or less, more preferably 2 mol or less, even more preferably 1.6 mol or less, especially preferably 1.3 mol or less.

An amount of (meth)acrylic acid set in a range of 0.1 mol to 5 mol relative to 1 mol of diphenyl carbonate increases the production of phenyl (meth)acrylate per unit volume of reactor.

When a catalyst is used in the embodiments of the present invention, the amount of catalyst is not limited specifically as long as phenyl (meth)acrylate is efficiently produced. Relative to 1 mol of diphenyl carbonate, the amount may be set in a range of 0.00001 mol to 4 mol, preferably 0.00005 mol to 1 mol, more preferably 0.0001 mol to 0.6 mol, even more preferably 0.001 mol to 0.3 mol, further more preferably 0.01 mol to 0.2 mol, especially preferably 0.03 mol to 0.15 mol, most preferably 0.05 mol to 0.1 mol.

An amount of catalyst set to be 0.00001 mol or greater relative to 1 mol of diphenyl carbonate effectively suppresses catalytic activity from decreasing as a result of impurities. An amount of catalyst set to be no greater than 4 mol relative to 1 mol of diphenyl carbonate efficiently prevents a decrease in the productivity of phenyl (meth)acrylate or in the purity level of the product.

A catalyst may or may not be dissolved in the reaction liquid, but it is preferred for the catalyst to be dissolved. A catalyst dissolved in the reaction liquid accelerates the production rate of the phenyl (meth)acrylate.

When the reaction of (meth)acrylic acid and diphenyl carbonate is carried out (hereinafter may also be referred to simply as "reaction"), a solvent may be used. However, from the viewpoint of productivity, it is preferred not to use a solvent. When a solvent is used, any type may be used unless it reacts with (meth)acrylic acid, diphenyl carbonate, a catalyst, or phenyl (meth)acrylate. Examples of a solvent are hydrocarbon solvents such as hexane, toluene, and xylene; ether solvents such as diethyl ether, and tetrahydrofuran; ketone solvents such as acetone, and methylethyl ketone; amide solvents such as dimethylformamide, and dimethylacetoamide. Those listed above may be used alone or in combination thereof.

Reaction temperature is not limited specifically, but it is preferred to be set in a range of 60° C. to 180° C., more preferably 80° C. to 160° C., even more preferably 95° C. to 150° C., especially preferably 110° C. to 140° C. The reaction progresses smoothly when the reaction temperature is 60° C. or higher, and polymerization or side reactions can be suppressed when the reaction temperature is set no higher than 180° C. Reaction temperature does not need to be set at a constant level, and it may vary within a preferred range.

The reaction time is not limited specifically, and may be selected appropriately according to the scale of reaction, reaction conditions or the like. Reaction time is preferred to be set for 1 hour or longer but 80 hours or shorter, preferably 2 hours or longer but 40 hours or shorter, more preferably 3 hours or longer but 20 hours or shorter. Reactions progress smoothly by setting a reaction time of 1 hour or longer, and polymerization or side reactions are suppressed when reaction time is set at 80 hours or shorter.

The pressure during reactions is not limited specifically, any of atmospheric pressure, reduced or compressed pressure conditions may be selected.

The type of reactors to carry out reactions is not limited specifically; examples are batch stirred-tank reactors, continuous stirred-tank reactors, continuous plug-flow reactors and the like. Among them, batch reactors are preferred.

The method for feeding reaction materials ((meth)acrylic acid, diphenyl carbonate, catalyst, solvent and the like) into a reactor is not limited specifically; they may be fed all at once before or during the heating process, part of or the entire material may be added by batch during the heating process, part of or the entire material may be added continuously, or a combination thereof may be used.

Especially, when feeding (meth)acrylic acid into the reactor, from the viewpoints of enhancing the reaction rate and productivity of phenyl (meth)acrylate, it is preferred to add (meth)acrylic acid by batch or continuously into a reaction liquid containing diphenyl carbonate and a catalyst when a catalyst is used. Continuous feeding is more preferred. Here, adding by batch means (meth)acrylic acid is divided into two or more portions and added to the reaction liquid accordingly. Adding continuously means (meth)acrylic acid is continuously added to the reaction liquid by dropping the (meth)acrylic acid or the like. Continuous feeding may be divided into two or more time frames.

When (meth)acrylic acid is added by batch, the amount in each batch may be constant or varied. However, it is preferred to reduce the amount at either of two consecutive feeding times, more preferably at both of two consecutive feeding times. Also, the feeding intervals may be constant, incremented or reduced, but setting constant or incremented intervals, more preferably incremented intervals, is preferred.

When (meth)acrylic acid is added continuously, the feeding rate may be constant, incremented or reduced. However, it is preferred to reduce the feeding rate in some of the continuous feeding time frames. Also, it is preferred to set the feeding rate to be constant or to be reduced during all the feeding time frames.

When (meth)acrylic acid is added by batch or continuously, the concentration of (meth)acrylic acid in the reaction liquid is not limited specifically. It may be constant or varied. However, the concentration is preferred to be low at least in some of the reaction time frames, more preferably during all of the time frames. In particular, a low concentration of (meth)acrylic acid means that when the molar number of (meth)acrylic acid in the reaction liquid is divided by the total molar numbers of diphenyl carbonate and phenyl (meth)acrylate, the value (molar ratio) is 0.0001 to 1. The molar ratio is preferred to be set in a range of 0.0001 to 0.8, more preferably 0.0001 to 0.6, even more preferably 0.0001 to 0.4, especially preferably 0.0001 to 0.2.

When (meth)acrylic acid is added by batch or continuously, the temperature of the reaction liquid is not limited specifically, but it is preferred to be set in a range of 60° C. to 180° C., more preferably 80° C. to 160° C., even more preferably 95° C. to 150° C., especially preferably 110° C. to 140° C.

The duration for adding (meth)acrylic acid by batch or continuously is not limited specifically, but it is preferred to be at least 30 minutes, more preferably at least 60 minutes, even more preferably at least 90 minutes, especially preferably at least 120 minutes.

When (meth)acrylic acid is added by batch or continuously, the reaction rate is enhanced compared with the method for feeding (meth)acrylic acid all at once. Moreover, side reaction products, for example, MAA adducts, PhOH adducts, phenyl methacrylate dimers, AA adducts and PHA-PhOH adducts, are suppressed, thereby increasing the production of phenyl (meth)acrylate.

While reactions are in progress or reaction products are being purified, and when solutions containing reaction products and purified phenyl (meth)acrylate solutions are stored, it is preferred to set the gas phase of the reactor to be an oxygen-containing gas ambient to prevent polymerization of raw material or reaction products. It is more preferred to blow an oxygen-containing gas such as oxygen and air into the reaction liquid. Such an oxygen-containing gas may be introduced from two or more parts of the reactor.

In addition, it is preferred to add a polymerization inhibitor in the reaction liquid so that the polymerization inhibitor coexists in the reaction liquid. Examples of an inhibitor are not limited to any specific types; for example, quinone inhibitor such as benzoquinone; phenolic inhibitors such as phenol, 1,4-benzendiol, 4-methoxyphenol, 2,6-di-tert-butylphenol, 2,4-di-tert-butylphenol, 2-tert-butyl-4,6-dimethylphenol, 2,6-di-tert-butyl-4-methylphenol, and 2,4,6-tri-tert-butylphenol; amine inhibitors such as alkylated diphenylamine, N,N'-diphenyl-p-phenylenediamine, and phenothiazine; N-oxyl inhibitors such as 4-hydroxy-2,2,6,6-tetramethylpiperidine-N-oxyl (HO-TEMPO), 4-benzoyloxy-2,2,6,6-tetramethylpiperidine-N-oxyl (BTOX), and 4-acetoxy-2,2,6,6-tetramethylpiperidine-N-oxyl; and copper dithiocarbamate inhibitors such as metallic copper, copper sulfate, copper dimethyldithiocarbamate, copper diethyldithiocarbamate, and copper dibutyldithiocarbamate. Among those listed above, phenol, 1,4-benzendiol, 4-methoxyphenol, phenothiazine, HO-TEMPO, and BTOX are preferred; more preferably phenol, 1,4-benzendiol, 4-methoxyphenol and BTOX; even more preferably phenol. Those polymerization inhibitors may be used alone or in combination thereof.

(5) Purification of Phenyl (meth)acrylate

Phenyl (meth)acrylate obtained in the embodiments of the present invention may be purified if applicable. The purification method is not limited specifically, and any known method may be employed.

To purify phenyl (meth)acrylate, separation, distillation, crystallization and the like may be used. Such methods may be conducted alone or in combination thereof. Phenyl (meth)acrylate is preferred to be purified by separation and distillation.

When phenyl (meth)acrylate is extracted through separation, alkaline solutions such as sodium hydroxide solutions and potassium hydroxide solutions may be used. The alkali concentration of the alkaline solution and the number of extractions may be selected appropriately according to reaction conditions or the like.

The distillation method is not limited specifically; for example, simple distillation, superfractionation, thin film distillation and the like may be employed. Distillation may be conducted under atmospheric pressure, reduced or compressed pressure, but distillation under reduced pressure is preferred.

(6) Phenyl (meth)acrylate Composition

A phenyl (meth)acrylate composition related to the present invention (hereinafter may also be referred to as a first composition) contains phenyl (meth)acrylate in a range of 90 mass % to 99.999 mass % and diphenyl carbonate in a range of 0.001 mass % to 10 mass %. The first composition is preferred to contain phenyl (meth)acrylate in a range of 95 mass % to 99.999 mass % and diphenyl carbonate in a range of 0.001 mass % to 5 mass %; more preferably, phenyl (meth)acrylate in a range of 98 mass % to 99.999 mass % and diphenyl carbonate in a range of 0.001 mass % to 2 mass %; even more preferably, phenyl (meth)acrylate in a range of 99 mass % to 99.999 mass % and diphenyl carbonate in a range of 0.001 mass % to 1 mass %; especially preferably, phenyl (meth)acrylate in a range of 99.5 mass % to 99.999 mass % and diphenyl carbonate in a range of 0.001 mass % to 0.5 mass %.

Setting the first composition to contain phenyl (meth)acrylate in a range of 90 mass % to 99.999 mass % suppresses impact on physical properties of a polymer. In addition, setting the first composition to contain diphenyl carbonate in a range of 0.001 mass % to 10 mass % suppresses polymerization during storage and makes it easier to handle the composition. Even when phenyl (meth)acrylate is not sufficiently purified to cause the catalyst to remain, diphenyl carbonate contained in a range of 0.001 mass % to 10 mass % will suppress unexpected polymerization from occurring. The first composition may contain phenyl (meth)acrylate in a range of 90 mass % to 99.999 mass % and diphenyl carbonate in a range of 0.001 mass % to 10 mass %. Namely, the total mass of phenyl (meth)acrylate and diphenyl carbonate may be 100 mass % of the first composition.

The first composition is appropriately produced by the production method of phenyl (meth)acrylate related to the present invention. The contents of phenyl (meth)acrylate and diphenyl carbonate may be adjusted within the ranges described in the embodiments of the present invention by modifying the catalyst and reaction time.

Another phenyl (meth)acrylate composition related to the present invention (hereinafter may also be referred to as a second composition) contains phenyl (meth)acrylate in a range of 90 mass % to 99.999 mass % and (meth)acrylic-acid adduct in a range of 0.001 mass % to 10 mass %. The second composition is preferred to contain phenyl (meth)acrylate in a range of 95 mass % to 99.999 mass % and (meth)acrylic-acid adduct in a range of 0.001 mass % to 5 mass %; more preferably, phenyl (meth)acrylate in a range of 98 mass % to 99.999 mass % and (meth)acrylic-acid adduct in a range of 0.001 mass % to 2 mass %; even more preferably, phenyl (meth)acrylate in a range of 99 mass % to 99.999 mass % and (meth)acrylic-acid adduct in a range of 0.001 mass % to 1 mass %; especially preferably, phenyl (meth)acrylate in a range of 99.5 mass % to 99.999 mass % and (meth)acrylic-acid adduct in a range of 0.001 mass % to 0.5 mass %.

Setting the second composition to contain phenyl (meth)acrylate in a range of 90 mass % to 99.999 mass % suppresses impact on the physical properties of a polymer. In addition, by setting the second composition to contain (meth)acrylic-acid adduct having a longer molecular chain than that of phenyl (meth)acrylate in a range of 0.001 mass % to 10 mass %, the melting point of the phenyl (meth) acrylate composition is lowered, thus preventing the composition from freezing in cold regions and making it easier to handle. The second composition may contain phenyl (meth)acrylate in a range of 90 mass % to 99.999 mass % and (meth)acrylic-acid adduct in a range of 0.001 mass % to 10 mass %. Namely, the total mass of phenyl (meth)acrylate and (meth)acrylic-acid adduct may be 100 mass % of the second composition.

The second composition is appropriately produced by the production method of phenyl (meth)acrylate related to the present invention. The contents of phenyl (meth)acrylate and (meth)acrylic acid adduct may be adjusted within the ranges described in the embodiments of the present invention by modifying the feeding method of (meth)acrylic acid into the reactor, for example.

The storage vessel for first and second compositions is not limited specifically; for example, glass vessels, resin vessels, metallic storage tanks, drums, lorries and the like may be used.

Usage purposes of the first and second compositions are not limited specifically. For example, they may be used as food additives, cosmetics additives, pharmaceutical materials, flavorings, synthetic resin materials, resin additives, coating materials, and so forth.

EXAMPLES

The present invention is further described in detail by referring to examples. However, the present invention is not limited to the examples below.

In the examples, diphenyl carbonate, phenyl (meth)acrylate and the like were analyzed through liquid chromatography or gas chromatography.

In the examples, the following were used: 99 mass % purity diphenyl carbonate purchased from Tokyo Chemical Industry Co., Ltd.; 99.9 mass % purity methacrylic acid, made by Mitsubishi Rayon Co., Ltd.; and 98 mass % purity acrylic acid made by Wako Pure Chemical Industries, Ltd.

Example 1

In a 200 mL glass vessel equipped with an air inlet, added were 25.8 grams (300 mmol) of methacrylic acid, 40.0 grams (187 mmol) of diphenyl carbonate, 0.6 grams (6 mmol) of sodium methacrylate as a catalyst, 0.02 grams of 1,4-benzendiol and 0.02 grams of 4-benzoyloxy-2,2,6,6-tetramethylpiperidine-N-oxyl as polymerization inhibitors. While air was being blown into the mixture at a rate of 10 mL/min, the mixture was heated to an internal temperature of 140° C. and stirred for 6 hours.

As a result, the conversion rate of diphenyl carbonate was 45% in the reaction liquid. The amount of produced phenyl methacrylate was 13.6 grams (84 mmol). The yield of phenyl methacrylate relative to diphenyl carbonate was 45%.

Examples 2~14

The same procedures were employed as in Example 1 except that 0.6 grams (6 mmol) of sodium methacrylate was not used; instead, the types and amounts (amount of charge) of catalyst respectively set as shown in Table 1 were used. The conversion rate of the obtained diphenyl carbonate in the reaction liquid, produced amount of phenyl methacrylate, and yield of phenyl methacrylate relative to diphenyl carbonate were also shown in Table 1. In the table, DPC means diphenyl carbonate, and PHMA means phenyl methacrylate.

TABLE 1

| | Catalyst | | | Reaction Result | | |
|---|---|---|---|---|---|---|
| | type | amount of charge (g) | amount of charge (mmol) | conversion rate of DPC (%) | produced amount of PHMA (g) | yield of PHMA relative to DPC (%) |
| Example 1 | sodium methacrylate | 0.6 | 6 | 45 | 13.6 | 45 |
| Example 2 | sodium phenoxide | 0.7 | 6 | 46 | 14.0 | 46 |
| Example 3 | lithium methacrylate | 0.5 | 6 | 47 | 14.2 | 47 |
| Example 4 | potassium methacrylate | 0.7 | 6 | 42 | 11.5 | 38 |
| Example 5 | magnesium methacrylate | 1.1 | 6 | 95 | 25.0 | 83 |
| Example 6 | magnesium acetylacetonate dihydrate | 1.4 | 6 | 91 | 20.6 | 68 |
| Example 7 | calcium methacrylate | 1.2 | 6 | 61 | 17.9 | 59 |
| Example 8 | calcium acetylacetonate | 1.3 | 6 | 63 | 16.1 | 53 |
| Example 9 | 4-dimethylaminopyridine | 0.7 | 6 | 97 | 26.6 | 88 |
| Example 10 | 4-aminopyridine | 0.5 | 6 | 88 | 23.4 | 77 |
| Example 11 | 1-methylimidazole | 0.5 | 6 | 76 | 23.0 | 76 |
| Example 12 | samarium (III) trifluoromethanesulfonate | 3.3 | 6 | 63 | 17.9 | 59 |
| Example 13 | lanthanum (III) trifluoromethanesulfonate | 3.3 | 6 | 29 | 8.8 | 29 |
| Example 14 | scandium (III) trifluoromethanesulfonate | 2.8 | 6 | 50 | 9.1 | 30 |

From the examples shown above, it is found that phenyl methacrylate is efficiently obtained by using various catalysts (amine compounds, Group 1 metal compounds, Group 2 metal compounds, and metal trifluoromethanesulfonates).

Example 15

Into a 200 mL three-neck glass flask equipped with a Dimroth condenser and an air inlet, added were 45.0 grams (523 mmol) of methacrylic acid, 79.9 grams (373 mmol) of diphenyl carbonate, 4.9 grams (45 mmol) of sodium methacrylate as a catalyst, 0.04 grams of 1,4-benzendiol and 0.04 grams of 4-benzoyloxy-2,2,6,6-tetramethylpiperidine-N-oxyl as polymerization inhibitors.

While air was being blown into the mixture at a rate of 20 mL/min, the mixture was heated to an internal temperature of 130° C. and stirred for 26 hours. Accordingly, a reaction liquid was obtained to have a diphenyl carbonate concentration of no greater than 0.003 mass %.

The reaction liquid was transferred to a separation funnel, 19 grams of n-hexane and 42 grams of a 15 mass % sodium hydroxide solution were added, and it was shaken vigorously to make a mixture. The mixture was separated into oil and water layers after it was left standing. The water layer was separated from the lower part, and the same procedure was conducted without adding n-hexane to the oil layer so that the oil layer was extracted once with 60 grams of a 15 mass % sodium hydroxide solution, once with 40 grams of a 15 mass % sodium hydroxide solution, and twice with 50 grams of water.

After 0.02 grams of 4-benzoyloxy-2,2,6,6-tetramethylpiperidine-N-oxyl was added as a polymerization inhibitor to the extracted oil layer, n-hexane was distilled to concentrate the liquid by using an evaporator under conditions of 25° C. and 50 torr (6.7 kPa) while air was being introduced.

The obtained liquid was transferred to a 100 mL flask equipped with an air inlet, and distilled at a pressure of 1~2 torr (0.1~0.3 kPa) while air was being introduced. Accordingly, 99.9 mass % purity phenyl methacrylate was obtained as a distillate at 71~74° C.

From the example above, it is found that when sodium methacrylate is used as a catalyst, phenyl methacrylate can be isolated at a high purity level by conducting extraction and distillation.

Example 16

In a 300 mL four-neck glass flask equipped with a Dimroth condenser and an air inlet, added were 48.2 grams (560 mmol) of methacrylic acid, 100.3 grams (468 mmol) of diphenyl carbonate, 5.5 grams (28 mmol) of magnesium methacrylate as a catalyst, 0.02 grams of 1,4-benzendiol and 0.02 grams of 4-benzoyloxy-2,2,6,6-tetramethylpiperidine-N-oxyl as polymerization inhibitors. While air was being blown into the mixture at a rate of 10 mL/min, the mixture was heated to an internal temperature of 140° C. and stirred for 9 hours.

The mass of the reaction liquid was 132 grams at the time of reaction completion. The reaction liquid contained phenyl methacrylate at 52 mass %, phenol at 34 mass % and methacrylic acid at 5 mass %, and the rest was a magnesium compound or the like derived from the catalyst. The mass of diphenyl carbonate was no greater than 0.003 mass %.

The reaction liquid was transferred to a separation funnel, 23 grams of n-hexane and 55 grams of water were added, and it was shaken vigorously to make a mixture. The mixture was separated into oil and water layers after it was left standing. The water layer was separated from the lower part, and the same procedure was conducted without adding n-hexane to the oil layer so that the oil layer was extracted once with 55 grams of water, once with 50 grams of a 15 mass % sodium hydroxide solution, once with 100 grams of a 15 mass % sodium hydroxide solution, twice with 50 grams of a 15 mass % sodium hydroxide solution, and twice with 50 grams of water.

After 0.02 grams of 4-benzoyloxy-2,2,6,6-tetramethylpiperidine-N-oxyl was added as a polymerization inhibitor to the layer, n-hexane was distilled to concentrate the liquid by using an evaporator under conditions of 25° C. and 50 torr (6.7 kPa) while air was being introduced.

The obtained liquid was transferred to a 100 mL flask equipped with an air inlet, and distilled at a pressure of 2~11 torr (0.3~1.5 kPa) while air was being introduced. Accordingly, 99.6 mass % purity phenyl methacrylate was obtained as a distillate at 57~74° C. The distillate contained an MAA adduct at 0.029 mass %.

From the example above, it is found that when magnesium methacrylate is used as a catalyst, a high purity phenyl methacrylate is isolated by conducting extraction and distillation.

Example 17

In a 200 mL glass vessel equipped with an air inlet, added were 8.0 grams (93 mmol) of methacrylic acid, 40.0 grams (187 mmol) of diphenyl carbonate, 2.2 grams (11 mmol) of magnesium methacrylate as a catalyst, 0.02 grams of 1,4-benzendiol and 0.02 grams of 4-benzoyloxy-2,2,6,6-tetramethylpiperidine-N-oxyl as polymerization inhibitors, and 3.2 grams (19 mmol) of diphenyl ether as an internal standard substance. While air was being blown into the mixture at a rate of 10 mL/min, the mixture was heated to an internal temperature of 130° C. and stirred for 5 hours. As a result of the reaction, 14.0 grams (86 mmol) of phenyl methacrylate was produced.

Examples 18~21

The same procedures were conducted as in Example 17 except that each amount of methacrylic acid to be added into the glass flask was changed as shown in Table 2. The molar ratio of methacrylic acid relative to the amount of diphenyl carbonate, and the amount of phenyl methacrylate, produced during each elapsed hour of the heating process are also shown in Table 2. In the table, MAA means methacrylic acid, DPC means diphenyl carbonate, and PHMA means phenyl methacrylate.

TABLE 2

| | MAA | | | Reaction Result | | | | |
| | amount of charge (g) | amount of charge (mmol) | molar ratio to DPC | produced amount of PHMA (g) | | | | |
| | | | | after 1 hr. | after 2 hrs. | after 3 hrs. | after 4 hrs. | after 5 hrs. |
|---|---|---|---|---|---|---|---|---|
| Example 17 | 8.0 | 93 | 0.5 | 12.6 | 14.6 | 15.0 | 15.1 | 15.3 |
| Example 18 | 16.1 | 187 | 1.0 | 11.1 | 17.7 | 21.9 | 24.1 | 25.7 |

TABLE 2-continued

|  | MAA | | | Reaction Result | | | | |
|---|---|---|---|---|---|---|---|---|
|  | amount | amount | molar | produced amount of PHMA (g) | | | | |
|  | of charge (g) | of charge (mmol) | ratio to DPC | after 1 hr. | after 2 hrs. | after 3 hrs. | after 4 hrs. | after 5 hrs. |
| Example 19 | 19.3 | 224 | 1.2 | 10.2 | 17.3 | 21.0 | 23.6 | 25.2 |
| Example 20 | 32.2 | 374 | 2.0 | 8.4 | 14.2 | 18.4 | 21.0 | 23.1 |
| Example 21 | 48.2 | 560 | 3.0 | 6.4 | 11.2 | 15.0 | 17.7 | 20.0 |

From the examples above, it is found that a greater amount of phenyl methacrylate is produced by using (meth) acrylic acid at various molar ratios relative to the amount of diphenyl carbonate.

Example 22

In a 200 mL glass vessel equipped with an air inlet, added were 21.2 grams (246 mmol) of methacrylic acid, 44.0 grams (205 mmol) of diphenyl carbonate, 1.2 grams (6 mmol) of magnesium methacrylate as a catalyst, 0.006 grams of 1,4-benzendiol and 0.006 grams of 4-benzoyloxy-2,2,6,6-tetramethylpiperidine-N-oxyl as polymerization inhibitors, and 3.5 grams (21 mmol) of diphenyl ether as an internal standard substance. While air was being blown into the mixture at a rate of 10 mL/min, the mixture was heated to an internal temperature of 100° C. and stirred for 16 hours.

As a result, the conversion rate of diphenyl carbonate was 28.2% in the reaction liquid. The amount of produced phenyl methacrylate was 8.8 grams (54 mmol). The yield of phenyl methacrylate relative to diphenyl carbonate was 27%. In addition, the selectivity of phenyl methacrylate (the value obtained when the yield of phenyl methacrylate is divided by the conversion rate of diphenyl carbonate) was 94%.

Examples 23~26

The same procedures were conducted as in Example 22 except that each reaction temperature was modified to that shown in Table 3. The conversion rate of diphenyl carbonate in the reaction liquid, the amount of produced phenyl methacrylate, the yield of phenyl methacrylate produced relative to diphenyl carbonate, and the selectivity of phenyl methacrylate are also shown in Table 3. In the table, DPC means diphenyl carbonate, and PHMA means phenyl methacrylate.

TABLE 3

|  | Reaction Temp (° C.) | Conversion Rate of DPC (%) | Produced Amount of PHMA (g) | Yield of PHMA relative to DPC (%) | Selectivity of PHMA (%) |
|---|---|---|---|---|---|
| Example 22 | 100 | 28.2 | 8.8 | 27 | 94 |
| Example 23 | 120 | 83.9 | 25.2 | 76 | 91 |
| Example 24 | 130 | 98.7 | 29.3 | 88 | 89 |
| Example 25 | 135 | 99.9 | 28.5 | 86 | 86 |
| Example 26 | 140 | 100.0 | 27.4 | 82 | 82 |

From the examples above, it is found that phenyl methacrylate is obtained at a significantly high level of selectivity even when reaction temperatures are set at various levels.

Example 27

Into a 200 mL glass vessel equipped with an air inlet, added were 21.2 grams (246 mmol) of methacrylic acid, 44.0 grams (205 mmol) of diphenyl carbonate, 2.4 grams (12 mmol) of magnesium methacrylate as a catalyst, 0.001 grams of phenol as a polymerization inhibitor, and 3.5 grams (21 mmol) of diphenyl ether as an internal standard substance. While air was being blown into the mixture at a rate of 10 mL/min, the mixture was heated to an internal temperature of 130° C. and stirred for 5 hours.

As a result, the conversion rate of diphenyl carbonate was 89% in the reaction liquid. The amount of produced phenyl methacrylate was 27.9 grams (172 mmol). The yield of phenyl methacrylate relative to diphenyl carbonate was 84%.

From the example above, it is found that phenyl methacrylate is obtained at a high yield even when the polymerization inhibitor is changed to phenol from 1,4-benzendiol and 4-benzoyloxy-2,2,6,6-tetramethylpiperidine-N-oxyl.

Example 28

In a 50 mL three-neck glass flask equipped with an air inlet, added were 6.5 grams (90 mmol) of acrylic acid, 16.0 grams (75 mmol) of diphenyl carbonate, 0.5 grams (4 mmol) of 4-dimethylaminopyridine as a catalyst, 0.004 grams of phenol as a polymerization inhibitor, and 1.3 grams (7 mmol) of diphenyl ether as an internal standard substance. While air was being blown into the mixture at a rate of 10 mL/min, the mixture was heated to an internal temperature of 130° C. and stirred for 6 hours. Then the mixture was heated to an internal temperature of 140° C. and stirred for 3 hours.

As a result, the amount of produced phenyl acrylate was 6.5 grams (44 mmol). The yield of phenyl acrylate relative to diphenyl carbonate was 59%.

From the example above, it is found that phenyl ester is obtained efficiently even when the material is changed from methacrylic acid to acrylic acid.

Example 29

In a 200 mL glass vessel equipped with an air inlet, added were 21.2 grams (246 mmol) of methacrylic acid, 44.0 grams (205 mmol) of diphenyl carbonate, 3.6 grams (18 mmol) of magnesium methacrylate as a catalyst, 0.006 grams of 1,4-benzendiol and 0.006 grams of 4-benzoyloxy-2,2,6,6-tetramethylpiperidine-N-oxyl as polymerization inhibitors, and 3.5 grams (21 mmol) of diphenyl ether as an internal standard substance. While air was being blown into the mixture at a rate of 10 mL/min, the mixture was heated to an internal temperature of 130° C. and stirred for 5 hours.

As a result, the conversion rate of diphenyl carbonate was 95% in the reaction liquid. The amount of produced phenyl methacrylate was 29.3 grams (180 mmol). The yield of phenyl methacrylate relative to diphenyl carbonate was 88%. In addition, the selectivity of phenyl methacrylate (the value obtained when the yield of phenyl methacrylate is divided by the conversion rate of diphenyl carbonate) was 93%.

From the example above, it is found that an increase in the amount of magnesium methacrylate as a catalyst will produce phenyl ester more efficiently.

Example 30

In a 50 mL three-neck glass flask equipped with an air inlet, added were 11.2 grams (131 mmol) of methacrylic acid, 23.2 grams (108 mmol) of diphenyl carbonate, 1.4 grams (13 mmol) of sodium methacrylate as a catalyst, 0.01 grams of 4-hydroxy-2,2,6,6-tetramethylpiperidine-N-oxyl and 0.01 grams of 4-benzoyloxy-2,2,6,6-tetramethylpiperidine-N-oxyl as polymerization inhibitors. While air was being blown into the mixture at a rate of 10 mL/min, the mixture was heated to an internal temperature of 130° C. and stirred for 3.0 hours.

As a result, the conversion rate of diphenyl carbonate was 59% in the reaction liquid. The amount of produced phenyl methacrylate was 10.1 grams (62 mmol). The yield of phenyl methacrylate relative to diphenyl carbonate was 58%.

Examples 31, 32

The same procedures were conducted as in Example 30 except that each amount of sodium methacrylate to be added to the flask was changed as shown in Table 4 and the heating time was changed to the duration shown in Table 4. The molar ratio of sodium methacrylate as a catalyst relative to the amount of diphenyl carbonate, heating time, conversion rate of diphenyl carbonate in the reaction liquid, amount of produced phenyl methacrylate, and yield of phenyl methacrylate relative to diphenyl carbonate are also shown in Table 4. In the table, DPC means diphenyl carbonate, and PHMA means phenyl methacrylate.

mmol) of sodium methacrylate as a catalyst, 0.02 grams of 1,4-benzendiol and 0.02 grams of 4-benzoyloxy-2,2,6,6-tetramethylpiperidine-N-oxyl as polymerization inhibitors. While air was being blown into the mixture at a rate of 10 mL/min, the mixture was heated to an internal temperature of 140° C. and stirred for 3.5 hours.

As a result, the conversion rate of diphenyl carbonate was 36% in the reaction liquid. The amount of produced phenyl methacrylate was 11.5 grams (71 mmol). The yield of phenyl methacrylate relative to diphenyl carbonate was 35%.

Example 34

In a 200 mL glass vessel equipped with an air inlet, added were 12.3 grams (143 mmol) of methacrylic acid, 43.0 grams (201 mmol) of diphenyl carbonate, 0.7 grams (6 mmol) of sodium methacrylate as a catalyst, 0.02 grams of 1,4-benzendiol and 0.02 grams of 4-benzoyloxy-2,2,6,6-tetramethylpiperidine-N-oxyl as polymerization inhibitors. While air was being blown into the mixture at a rate of 10 mL/min, the mixture was heated and stirred to an internal temperature of 140° C. The time when the internal temperature had reached 140° C. was set at zero, and 1.7 grams (20 mmol) of methacrylic acid was added at each elapsed time of 0.5 hours, 1.0 hour, 1.5 hours, 2.0 hours, 2.5 hours and 3.0 hours. The total amount of supplied methacrylic acid was 22.6 grams (263 mmol). The mixture was stirred for an elapsed healing time of 3.5 hours.

As a result, the conversion rate of diphenyl carbonate was 45% in the reaction liquid. The amount of produced phenyl methacrylate was 14.5 grams (89 mmol). The yield of phenyl methacrylate relative to diphenyl carbonate was 45%.

The conversion rate of diphenyl carbonate in the reaction liquid, the amount of produced phenyl methacrylate, and the yield of phenyl methacrylate relative to diphenyl carbonate are also shown in Table 5. In the table, DPC means diphenyl carbonate, and PHMA means phenyl methacrylate.

TABLE 4

| | Sodium Methacrylate | | | | Reaction Result | | |
| --- | --- | --- | --- | --- | --- | --- | --- |
| | | | | | conversion | produced | yield of PHMA |
| | amount of charge (g) | amount of charge (mmol) | molar ratio to DPC | Heating Time (h) | rate of DPC (%) | amount of PHMA (g) | relative to DPC (%) |
| Example 30 | 1.4 | 13 | 0.12 | 3.0 | 59 | 10.1 | 58 |
| Example 31 | 2.3 | 22 | 0.20 | 2.0 | 61 | 10.0 | 57 |
| Example 32 | 3.2 | 29 | 0.27 | 0.9 | 45 | 7.7 | 44 |

From the examples above, it is found that phenyl methacrylate is efficiently obtained even when the amount of sodium methacrylate is changed.

Example 33

In a 200 mL glass vessel equipped with an air inlet, added were 22.6 grams (263 mmol) of methacrylic acid, 43.0 grams (201 mmol) of diphenyl carbonate, 0.7 grams (6

TABLE 5

| | Conversion Rate of DPC (%) | Produced Amount of PHMA (g) | Yield of PHMA relative to DPC (%) |
| --- | --- | --- | --- |
| Example 33 | 36 | 11.5 | 35 |
| Example 34 | 45 | 14.5 | 45 |

From the examples above, it is found that the production rate of phenyl methacrylate is accelerated when reaction is carried out by adding methacrylic acid by batch.

Example 35

In a 200 mL glass vessel equipped with an air inlet, added were 21.2 grams (246 mmol) of methacrylic acid, 44.0 grams (205 mmol) of diphenyl carbonate, 2.4 grams (12 mmol) of magnesium methacrylate as a catalyst, 0.04 grams of phenol as a polymerization inhibitor, and 3.5 grams (21 mmol) of diphenyl ether as an internal standard substance. While air was being blown into the mixture at a rate of 10 mL/min, the mixture was heated to an internal temperature of 140° C. and stirred for 5 hours.

As a result, the conversion rate of diphenyl carbonate in the reaction liquid was 98.8%. The amount of produced phenyl methacrylate was 30.3 grams (187 mmol). The yield of phenyl methacrylate relative to diphenyl carbonate was 91%. The amount of produced MAA adduct was 1.05 grams (4.2 mmol). The yield of MAA adduct relative to diphenyl carbonate was 2.07%. The amount of produced PhOH adduct was 0.27 grams (1.1 mmol). The yield of PhOH adduct relative to diphenyl carbonate was 0.51%. The amount of produced phenyl methacrylate dimer was 0.84 grams (2.6 mmol). The yield of phenyl methacrylate dimer relative to diphenyl carbonate was 2.52%. The selectivity of phenyl methacrylate (the value obtained when the yield of phenyl methacrylate is divided by the conversion rate of diphenyl carbonate) was 92%.

Example 36

In a 200 mL glass vessel equipped with an air inlet, added were 9.2 grams (106 mmol) of methacrylic acid, 44.0 grams (205 mmol) of diphenyl carbonate, 2.4 grams (12 mmol) of magnesium methacrylate as a catalyst, 0.04 grams of phenol as a polymerization inhibitor, and 3.5 grams (21 mmol) of diphenyl ether as an internal standard substance. While air was being blown into the mixture at a rate of 10 mL/min, the mixture was heated and stirred to an internal temperature of 140° C. The time when the internal temperature had reached 140° C. was set at zero, 3.5 grams (40 mmol) of methacrylic acid was added at an elapsed time of 0.5 hours, and 1.7 grams (20 mmol) of methacrylic acid was added at each elapsed time of 1.0 hour, 1.5 hours, 2.0 hours, 2.5 hours and 3.0 hours. The total amount of supplied methacrylic acid was 21.2 grams (246 mmol). The mixture was stirred for an elapsed heating time of 5.0 hours.

As a result, the conversion rate of diphenyl carbonate in the reaction liquid was 98.9%. The amount of produced phenyl methacrylate was 30.7 grams (189 mmol). The yield of phenyl methacrylate relative to diphenyl carbonate was 92%. The amount of produced MAA adduct was 0.57 grams (2.3 mmol). The yield of MAA adduct relative to diphenyl carbonate was 1.12%. The amount of produced PhOH adduct was 0.19 grams (0.8 mmol). The yield of PhOH adduct relative to diphenyl carbonate was 0.37%. The amount of produced phenyl methacrylate dimer was 0.79 grams (2.4 mmol). The yield of phenyl methacrylate dimer relative to diphenyl carbonate was 2.38%. The selectivity of phenyl methacrylate (the value obtained when the yield of phenyl methacrylate is divided by the conversion rate of diphenyl carbonate) was 93%.

Example 37

In a 200 mL glass vessel equipped with an air inlet, added were 9.2 grams (106 mmol) of methacrylic acid, 44.0 grams (205 mmol) of diphenyl carbonate, 2.4 grams (12 mmol) of magnesium methacrylate as a catalyst, 0.04 grams of phenol as a polymerization inhibitor, and 3.5 grams (21 mmol) of diphenyl ether as an internal standard substance. While air was being blown into the mixture at a rate of 10 mL/min, the mixture was heated and stirred to an internal temperature of 140° C. The time when the internal temperature had reached 140° C. was set at zero, and 6.8 grams (80 mmol) of methacrylic acid was continuously added at a rate of 0.113 g/min during a time frame of 30~90 minutes. Also, 5.2 grams (60 mmol) of methacrylic acid was continuously added at a rate of 0.058 g/min during a time frame of 95~185 minutes. The total amount of supplied methacrylic acid was 21.2 grams (246 mmol). The mixture was stirred for an elapsed heating time of 5.0 hours.

As a result, the conversion rate of diphenyl carbonate in the reaction liquid was 99.0%. The amount of produced phenyl methacrylate was 30.9 grams (190 mmol). The yield of phenyl methacrylate relative to diphenyl carbonate was 93%. The amount of produced MAA adduct was 0.53 grams (2.1 mmol). The yield of MAA adduct relative to diphenyl carbonate was 1.04%. The amount of produced PhOH adduct was 0.20 grams (0.8 mmol). The yield of PhOH adduct relative to diphenyl carbonate was 0.39%. The amount of produced phenyl methacrylate dimer was 0.79 grams (2.4 mmol). The yield of phenyl methacrylate dimer relative to diphenyl carbonate was 2.38%. The selectivity of phenyl methacrylate (the value obtained when the yield of phenyl methacrylate is divided by the conversion rate of diphenyl carbonate) was 94%.

Table 6 shows the conversion rate of diphenyl carbonate in the reaction liquid, the amount of produced phenyl methacrylate, the yield of phenyl methacrylate relative to diphenyl carbonate, the yield of MAA adduct relative to diphenyl carbonate, the yield of PhOH adduct relative to diphenyl carbonate, and the yield of phenyl methacrylate dimer relative to diphenyl carbonate. In the table, DPC means diphenyl carbonate, PHMA means phenyl methacrylate, and MAA means methacrylic acid.

TABLE 6

|  | Conversion Rate of DPC (%) | Produced Amount of PHMA (g) | Yield of PHMA relative to DPC (%) | Yield of MAA Adduct relative to DPC (%) | Yield of PhOH Adduct relative to DPC (%) | Yield of PHMA Dimer relative to DPC (%) |
|---|---|---|---|---|---|---|
| Example 35 | 98.8 | 30.3 | 91 | 2.07 | 0.51 | 2.52 |
| Example 36 | 98.9 | 30.7 | 92 | 1.12 | 0.37 | 2.38 |
| Example 37 | 99.0 | 30.9 | 93 | 1.04 | 0.39 | 2.38 |

From the examples above, it is found that when reaction is carried out by adding methacrylic acid by batch or continuously, side reactions are suppressed, and the production of phenyl methacrylate is thereby increased.

Example 38

In a 1 L four-neck glass flask equipped with a Dimroth condenser and an air inlet, added were 193.1 grams (2.24 mol) of methacrylic acid, 400.0 grams (1.87 mol) of diphenyl carbonate, 21.8 grams (0.11 mol) of magnesium methacrylate as a catalyst, and 0.4 grams of phenol as a polymerization inhibitor.

While air was being blown into the mixture at a rate of 20 mL/min, the mixture was heated to have an internal temperature of 100° C. and stirred for 2 hours. Then, the mixture was heated to have an internal temperature of 120° C. and stirred for 2 hours, and further heated to have an internal temperature of 130° C. and stirred for 14 hours. As a result, 527.0 grams of reaction liquid was obtained.

The conversion rate of diphenyl carbonate in the reaction liquid was 99.5%. The amount of produced phenyl methacrylate was 268.3 grams (1.65 mol). The yield of phenyl methacrylate relative to diphenyl carbonate was 88%. The amount of produced MAA adduct was 11.1 grams (44.7 mmol). The yield of MAA adduct relative to diphenyl carbonate was 2.4%. The amount of produced PhOH adduct was 3.4 grams (13.3 mmol). The yield of PhOH adduct relative to diphenyl carbonate was 0.7%. The amount of produced phenyl methacrylate dimer was 8.5 grams (26.2 mmol). The yield of phenyl methacrylate dimer relative to diphenyl carbonate was 2.8%. The selectivity of phenyl methacrylate (the value obtained when the yield of phenyl methacrylate is divided by the conversion rate of diphenyl carbonate) was 88%.

The reaction liquid was transferred to a separation funnel, 120 grams of n-hexane and 150 grams of 9 mass % hydrogen chloride solution were added and it was shaken vigorously to make a mixture. The mixture was separated into oil and water layers after it was left standing. The water layer was separated from the lower part, and the same procedure was conducted without adding n-hexane to the oil layer so that the oil layer was extracted once with 100 grams of water, three times with 200 grams of a 15 mass % sodium hydroxide solution, and twice with 200 grams of water.

After 0.6 grams of phenothiazine was added as a polymerization inhibitor to the oil layer, n-hexane was distilled to concentrate the liquid by using an evaporator under conditions of 20° C. and 70~120 torr (9.3~16.0 kPa) while air was being introduced.

The liquid was purified through distillation by using a membrane distillation apparatus under conditions of medium temperature at 72° C., pressure at 0.7~0.8 torr (0.09~0.11 kPa), and flow rate at 3.6 mL/min. Accordingly, 227.6 grams (1.40 mol) of 99.7 mass % purity phenyl methacrylate was obtained as the distillate. The total yield relative to diphenyl carbonate was 75%. In addition, the distillate contained diphenyl carbonate at 0.050 mass %, phenol at 0.006 mass %, MAA adduct at 0.165 mass %, and PhOH adduct at 0.007 mass %.

From the example above, it is found that a high-purity phenyl methacrylate is also obtained through membrane distillation.

Example 39

Into a 30 mL glass tube, added was 5.6 grams of a composition containing phenyl methacrylate at 90.0 mass % and diphenyl carbonate at 10.0 mass %. When the mixture was heated in a 120° C. oil bath for 6 hours, no polymerization occurred and the mixture remained as a liquid.

Comparative Example 1

In a 30 mL glass tube, added was 5.0 grams of a composition that contained phenyl methacrylate at 99.9 mass % but no diphenyl carbonate. When the mixture was heated in a 120° C. oil bath for 6 hours, a solid product was obtained as a result of polymerization.

Examples 40~44

The same procedures were conducted as in Example 39 except that the contents of each glass tube were changed to those shown in Table 7. The state of the contents after heating is also shown in Table 7. In the table, DPC means diphenyl carbonate, and PHMA means phenyl methacrylate.

TABLE 7

|  | Contents | | | | | | | |
|---|---|---|---|---|---|---|---|---|
|  | PHMA Composition | | | | Additives | | | |
|  | composition ratio | amount of charge (g) | PHMA content (mmol) | DPC content (mmol) | name of compound | supplied amount (g) | supplied amount (mmol) | Condition of Content after Heating |
| Example 39 | PHMA: 90.0 mass % DPC: 10.0 mass % | 5.6 | 31 | 2.60 | — | — | — | liquid |
| Example 40 | PHMA: 90.0 mass % DPC: 10.0 mass % | 5.6 | 31 | 2.60 | 4-dimethylamino-pyridine | 0.300 | 2.60 | liquid |
| Example 41 | PHMA: 90.0 mass % DPC: 10.0 mass % | 5.6 | 31 | 2.60 | triphenylphosphine | 0.700 | 2.60 | liquid |
| Example 42 | PHMA: 90.0 mass % DPC: 10.0 mass % | 5.6 | 31 | 2.60 | magnesium oxide | 0.100 | 2.60 | liquid |
| Example 43 | PHMA: 99.8 mass % DPC: 0.2 mass % | 5.0 | 31 | 0.05 | 4-dimethylamino-pyridine | 0.006 | 0.05 | liquid |
| Example 44 | PHMA: 99.8 mass % DPC: 0.2 mass % | 5.0 | 31 | 0.05 | triphenylphosphine | 0.013 | 0.05 | liquid |
| Comp. Example 1 | PHMA 99.9 mass % | 5.0 | 31 | 0 | — | — | — | solid |

From the examples above, when a phenyl methacrylate composition contains diphenyl carbonate in a range of 0.001 mass % to 10 mass %, it is found that polymerization is suppressed.

Example 45

In a 50 mL three-neck glass flask equipped with an air inlet, added were 12.1 grams (168 mmol) of acrylic acid, 12.0 grams (56 mmol) of diphenyl carbonate, 0.34 grams (6 mmol) of magnesium hydroxide as a catalyst, 0.01 grams of phenol as a polymerization inhibitor, and 0.95 grams (5 mmol) of diphenyl ether as an internal standard substance. While air was being blown into the mixture at a rate of 10 mL/min, the mixture was heated to an internal temperature of 135° C. and stirred for 12 hours.

As a result, the amount of produced phenyl acrylate was 4.1 grams (28 mmol). The yield of phenyl acrylate relative to diphenyl carbonate was 49%.

Example 46

The same procedures were conducted as in Example 45 except that 0.34 grams (6 mmol) of magnesium hydroxide added to the flask was changed to 0.68 grams (6 mmol) of 4-dimethylaminopyridine. The amount of produced phenyl acrylate, and the yield of phenyl acrylate relative to diphenyl carbonate are also shown in Table 8. PHA in the table means phenyl acrylate.

TABLE 8

| | Catalyst | Produced Amount of PHA (g) | Yield of PHA (%) |
|---|---|---|---|
| Example 45 | magnesium hydroxide | 4.1 | 49 |
| Example 46 | 4-dimethylaminopyridine | 3.3 | 40 |

The present application is a Divisional of U.S. application Serial No. 15/025,507, filed Mar. 28, 2016, now pending; which is a 371 of PCT/JP2014/078338, fifed Oct. 24, 2014; and is based upon and claims the benefit of priority to Japanese Patent Application No. 2013-225352, filed Oct. 30, 2013. The entire contents of the application are incorporated herein by reference.

So far, the present invention has been described with reference to the embodiments and examples. However, the present invention is not limited to those embodiments and examples. Various modifications understandable to a person skilled in the art may be made within the scope of the present invention.

What is claimed is:

1. A phenyl (meth)acrylate composition, comprising:
    phenyl (meth)acrylate in a range of 90 mass % to 99.999 mass %; and
    diphenyl carbonate in a range of 0.001 mass % to 10 mass %.

2. The phenyl (meth)acrylate composition according to claim 1, comprising:
    phenyl (meth)acrylate in a range of 95 mass % to 99.999 mass %; and
    diphenyl carbonate in a range of 0.001 mass % to 5 mass %.

3. The phenyl (meth)acrylate composition according to claim 1, comprising:
    phenyl (meth)acrylate in a range of 98 mass % to 99.999 mass %; and
    diphenyl carbonate in a range of 0.001 mass % to 2 mass %.

4. The phenyl (meth)acrylate composition according to claim 1, comprising:
    phenyl (meth)acrylate in a range of 99 mass % to 99.999 mass %; and
    diphenyl carbonate in a range of 0.001 mass % to 1 mass %.

5. The phenyl (meth)acrylate composition according to claim 1, comprising:
    phenyl (meth)acrylate in a range of 99.5 mass % to 99.999 mass %; and
    diphenyl carbonate in a range of 0.001 mass % to 0.5 mass %.

6. The phenyl (meth)acrylate composition according to claim 1, wherein the total mass of phenyl (meth)acrylate and diphenyl carbonate is 100 mass % of the phenyl (meth)acrylate composition.

7. The phenyl (meth)acrylate composition according to claim 2, wherein the total mass of phenyl (meth)acrylate and diphenyl carbonate is 100 mass % of the phenyl (meth)acrylate composition.

8. The phenyl (meth)acrylate composition according to claim 3, wherein the total mass of phenyl (meth)acrylate and diphenyl carbonate is 100 mass % of the phenyl (meth)acrylate composition.

9. The phenyl (meth)acrylate composition according to claim 4, wherein the total mass of phenyl (meth)acrylate and diphenyl carbonate is 100 mass % of the phenyl (meth)acrylate composition.

10. The phenyl (meth)acrylate composition according to claim 5, wherein the total mass of phenyl (meth)acrylate and diphenyl carbonate is 100 mass % of the phenyl (meth)acrylate composition.

* * * * *